United States Patent [19]

Petrillo, Jr. et al.

[11] Patent Number: 4,873,356

[45] Date of Patent: Oct. 10, 1989

[54] METHOD FOR PREPARING PHOSPHINIC ACIDS USED IN PREPARING ACE INHIBITORS AND INTERMEDIATES PRODUCED THEREBY

[75] Inventors: Edward W. Petrillo, Jr., Pennington; Donald S. Karanewsky, East Windsor; John K. Thottathil, Lawrenceville; James E. Heikes, East Windsor; John A. Grosso, Princeton Junction, all of N.J.

[73] Assignee: E. R. Squibb & Sons, Inc., Princeton, N.J.

[21] Appl. No.: 102,694

[22] Filed: Sep. 30, 1987

[51] Int. Cl.$^4$ .............................................. C07F 9/32
[52] U.S. Cl. ..................................... 558/180; 558/179
[58] Field of Search ................................ 558/179, 180

[56] References Cited

U.S. PATENT DOCUMENTS

| | | | |
|---|---|---|---|
| 4,396,772 | 8/1983 | Petrillo, Jr. | 548/112 |
| 4,448,772 | 5/1984 | Karanewsky | 548/414 |
| 4,468,519 | 8/1984 | Krapcho | 548/413 |

*Primary Examiner*—Jacqueline V. Howard
*Attorney, Agent, or Firm*—Burton Rodney

[57] ABSTRACT

A method is provided for preparing phosphinic acid compounds, which are useful in preparing certain angiotensin converting enzyme inhibitors, which have the formula

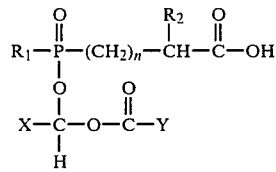

wherein
$R_1$ is lower alkyl, aryl, arylalkyl, cycloalkyl or cycloalkylalkyl;
$R_2$ is hydrogen, lower alkyl or arylalkyl;
X is hydrogen, lower alkyl or phenyl;
Y is hydrogen, lower alkyl, phenyl or alkoxy, or together X and Y are —(CH$_2$)$_2$—, —(CH$_2$)$_3$—, —CH=CH—, or

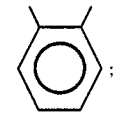

and
n is 0 or 1
including salts thereof and stereoisomers thereof, which method includes the steps of reacting a phosphinic acid ester of the structure

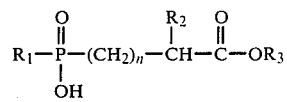

wherein $R_3$ is a group removable by hydrogenolysis such as benzyl or substituted benzyl, with a halo ester of the structure

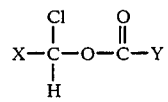

in the presence of an organic base to form a phosphinic acid ester of the structure

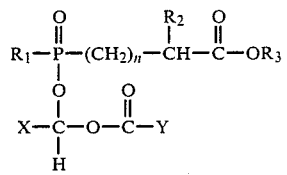

hydrogenating the above ester to form a diastereomic mixture of a phosphinic acid of the structure

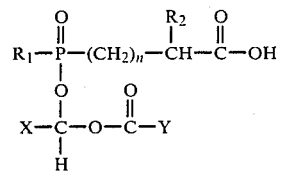

recrystallizing to recover the preferred racemic mixture and resolving same employing a resolving agent, preferably L-cinchonidine, to form the corresponding resolved salt which may be acidified to the corresponding acid. In addition, novel intermediates which are acids and salts as described above are also provided.

9 Claims, No Drawings

METHOD FOR PREPARING PHOSPHINIC ACIDS USED IN PREPARING ACE INHIBITORS AND INTERMEDIATES PRODUCED THEREBY

FIELD OF THE INVENTION

A method is provided for preparing phosphinic acid compounds which have the formula

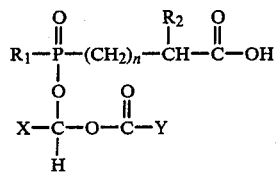   I wherein
$R_1$ is lower alkyl, aryl, arylalkyl, cycloalkyl or cycloalkylalkyl;
$R_2$ is hydrogen, lower alkyl or arylalkyl;
X is hydrogen, lower alkyl or phenyl;
Y is hydrogen, lower alkyl, phenyl or alkoxy, or together X and Y are —$(CH_2)_2$—, —$(CH_2)_3$—, —CH=CH—, or

and
n is 0 or 1
including salts thereof and stereoisomers thereof, which are useful in preparing certain angiotensin converting enzyme inhibitors, such as disclosed in U.S. Pat. No. 4,337,201 to Petrillo. In addition, new intermediates as described below are also provided.

BACKGROUND OF THE INVENTION

U.S. Pat. No. 4,602,092 to Thottathil et al discloses a method for preparing phosphinic acid intermediates having the structure

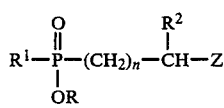

wherein
R is H or lower alkyl;
$R^1$ is lower alkyl, aryl, arylalkyl, cycloalkyl, or cycloalkylalkyl; $R^2$ is H or lower alkyl; Z is H, lower alkyl, —$CO_2R^3$ (wherein $R^3$ is H, lower alkyl or arylalkyl),

(wherein $R^4$ is H, lower alkyl, aryl or arylalkyl), —CN, or

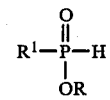

(wherein $R^5$ and $R^6$ are the same or different and can be hydrogen, lower alkyl, aryl, aryl-lower alkyl, cycloalkyl or cycloalkylalkyl, and at least one of $R^5$ and $R^6$ is other than hydrogen, or $R^5$ and $R^6$ can be taken together with the nitrogen atom to form a 5-, 6- or 7-membered heterocyclic ring,

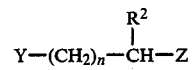

which method includes the step of reacting a phosphonous acid or ester of the structure $$R^1-\overset{\overset{O}{\|}}{\underset{OR}{P}}-H$$

wherein R and $R^1$ are as defined above, with an alkylating agent of the structure $$Y-(CH_2)_n-\overset{R^2}{\underset{}{C}}H-Z$$

wherein Y is a leaving group such as halogen including Cl, Br or F, mesyloxy or toxyloxy, and n, $R^2$ and Z are as defined above.

U.S. Pat. No. 4,337,201 to Petrillo discloses phosphinylalkanoyl substituted prolines which are angiotensin converting enzyme inhibitors, and have the formula

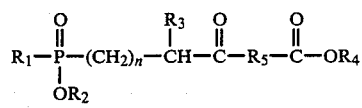

and salts thereof,
wherein
$R_1$ is alkyl, aryl, arylalkyl, cycloalkyl, or cycloalkyl(alkyl);
$R_2$ and $R_4$ each is independently hydrogen, alkyl, arylalkyl or

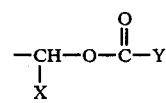

wherein X is hydrogen, alkyl, or phenyl and Y is hydrogen, alkyl, phenyl or alkoxy, or together X and Y are —$(CH_2)_2$—, —$(CH_2)_3$—, —CH=CH—, or

$R_3$ is hydrogen or alkyl;

$-R_5-COOR_4$ is

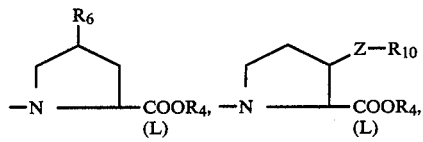

$R_6$ is hydrogen, hydroxy, alkyl, halogen, azido, amino, cycloalkyl, aryl, arylalkyl, carbamoyloxy $$(-O-\overset{O}{\underset{\|}{C}}-NH_2),$$

N,N-dialkylcarbamoyloxy, or $-Z-R_9$;

$R_7$ and $R_{7'}$ are the same and each is halogen or $-Z-R_{10}$, or $R_7$ and $R_{7'}$ together are $=O$, $-O-(CH_2)_m-O-$ or $-S-(CH_2)_m-S-$;

$R_8$ is hydrogen and $R_{8'}$ is phenyl, 2-hydroxyphenyl or 4-hydroxyphenyl or $R_8$ and $R_{8'}$ together are $=O$;

$R_9$ is alkyl, aryl, arylalkyl, 1- or 2-naphthyl, or biphenyl;

$R_{10}$ is alkyl, aryl or arylalkyl;

Z is oxygen or sulfur;

n is 0 or 1; and m is 1 or 2; with the proviso that if $-R_5-COOR_4$ is

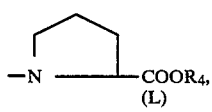

at least one or $R_2$ and $R_4$ is

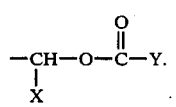

Included among the above compounds is fosinopril, that is

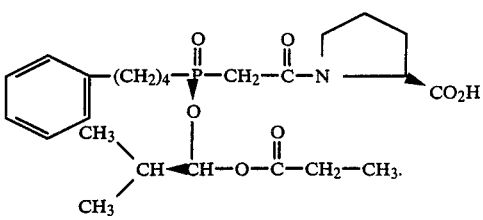

As described, the above phosphinylalkanoyl substituted prolines can be prepared by reacting a proline derivative having the formula

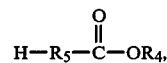

wherein $R_4$, is alkyl, arylalkyl or

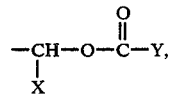

with a phosphinyl-acetic or propionic acid having the formula

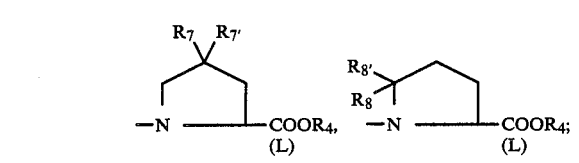

to form

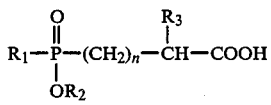

The reaction is accomplished using known amide bond forming procedures. For example, the reaction can be run in the presence of a coupling agent such as dicyclohexylcarbodiimide, or the above acid can be activated by formation of its mixed anhydride, symmetrical anhydride, acid halide (preferably acid chloride) or acid ester, or by the use of Woodward reagent K, N-ethoxycarbonyl-2-ethoxy-1,2-dihydroquinoline, N,N'-carbonyldiimidazole or the like. A review of these methods can be found in *Methoden der Organischem Chemie* (Houben-Weyl), Vol. XV, part II, page 1 et seq. (1974).

DESCRIPTION OF THE INVENTION

In accordance with the present invention, a method is provided for preparing a compound having the structure IA

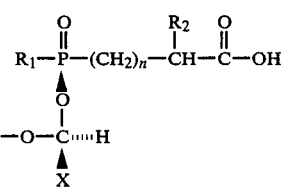

including salts thereof, and all stereoisomers thereof, wherein
R$_1$ is lower alkyl, aryl, arylalkyl, cycloalkyl or cycloalkylalkyl;
R$_2$ is hydrogen, lower alkyl or arylalkyl;
X is hydrogen, lower alkyl or phenyl;
Y is hydrogen, lower alkyl, phenyl or alkoxy, or together X and Y are —(CH$_2$)$_2$, —(CH$_2$)$_3$—, —CH=CH or

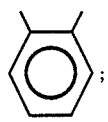

and
n is 0 or 1,
which method includes the steps of reacting a phosphinic acid ester of the structure II

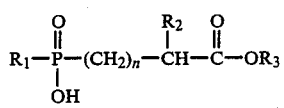

wherein R$_3$ is a group removable via hydrogenolysis and is benzyl or substituted benzyl such as

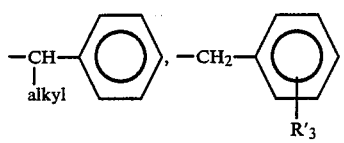

wherein R'$_3$ is alkyl, alkoxy, alkanoyl, phenyl or dialkylamino which may be substituted at the o, m or p-position, with a halo ester of the structure III

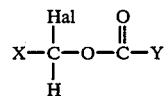

wherein Hal is Cl or Br and X and Y are as defined above, in the presence of an organic base to form a phosphinic acid ester of the structure IV,

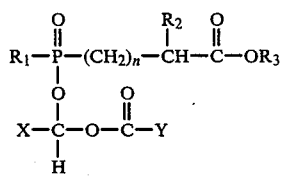

hydrogenating the phosphinic acid ester IV by treating with hydrogen in the presence of a hydrogenation catalyst, such as palladium on charcoal, or other conventional palladium catalysts, to form a pair of racemic mixtures of compounds (or a mixture of two diastereomers) of the structure

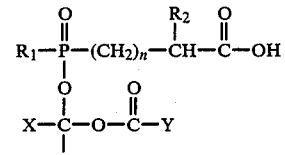

that is, a mixture of

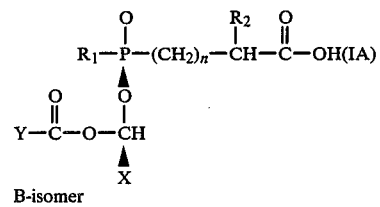

B-isomer

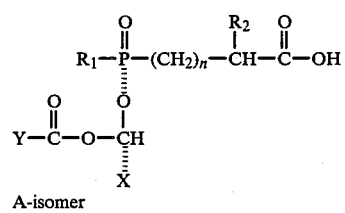

A-isomer

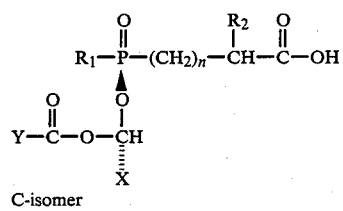

C-isomer

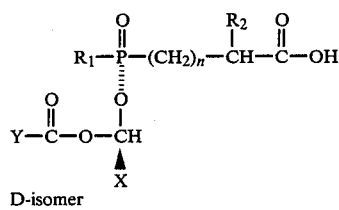

D-isomer separating out, for example, by recrystallization, for example using isobutyl acetate or methyl isobutyl ketone, the racemic mixture of

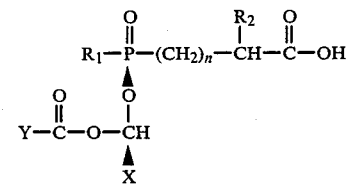

and

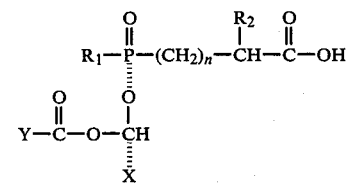

and resolving the racemic mixture by treating with a resolving agent, such as L-cinchonidine or other conventional resolving agent (optically active amine), to form the resolved salt of the structure

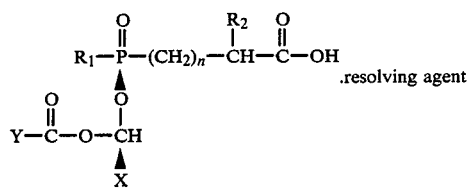 .resolving agent

The resolved salt II, such as

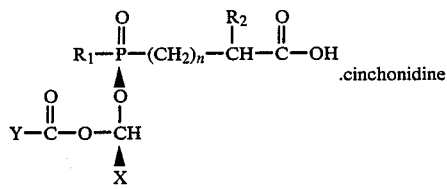 .cinchonidine may be treated with a strong acid or acid salt, such as potassium hydrogen sulfate, hydrochloric acid or sulfuric acid to form the acid IA.

The reaction of phosphinic acid ester III with the halo ester III may be carried out in the presence of an organic base such as triethylamine, pyridine, tripropylamine, diazabicycloundecene (DBU) or any other common organic bases, with triethylamine being preferred, and an organic solvent such as toluene, chloroform, acetonitrile, dichloromethane, ethyl ether, tetrahydrofuran or dioxane, with toluene being preferred, and optionally in the presence of a catalyst such as tetrabutylammonium sulfate and sodium iodide.

The phosphinic acid ester II will be employed in a molar ratio to the halo ester III of within the range of from about 0.1:1 to about 1:1 and preferably from about 0.2:1 to about 0.3:1 and the reaction of II and III will be carried out at a temperature of within the range of from about 50° to about 130° C. for a period of from about 2 to about 12 hours.

The racemic mixture (IA-IB), prepared by hydrogenolysis of the ester IV followed by fractional crystallization, is resolved by treating the racemic mixture of IA and IB with a resolving agent such as L-cinchonidine or other optically active amine, with L-cinchonidine being preferred, in the presence of an inert organic solvent such as ethyl acetate, ethyl alcohol or tetrahydrofuran with ethyl acetate being preferred. The above reaction will be carried out at a temperature within the range of from about 25° to about 80° C. for a period of from about 2 to about 12 hours with the resolving agent being employed in a molar ratio to the racemic mixture of IA and IB of within the range of from about 2:1 to about 0.2:1 and preferably from about 1:1 to about 0.5:1.

The intermediates V

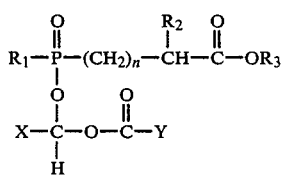 V including all stereoisomers thereof, such as

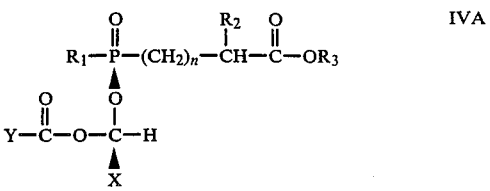 IVA for example

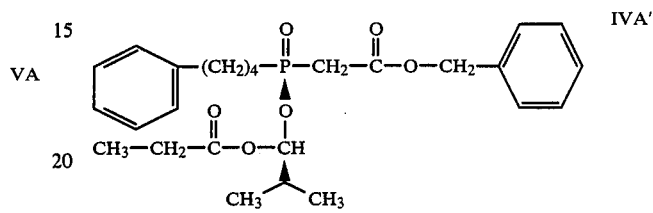 IVA' the intermediate

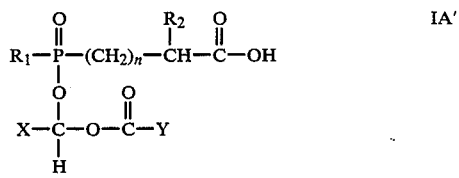 IA' including all stereoisomers thereof, such as

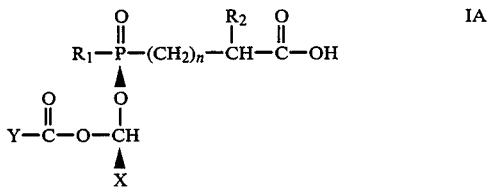 IA for example,

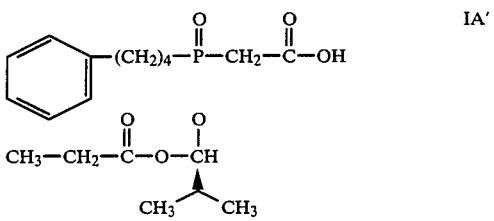 IA' and the intermediate

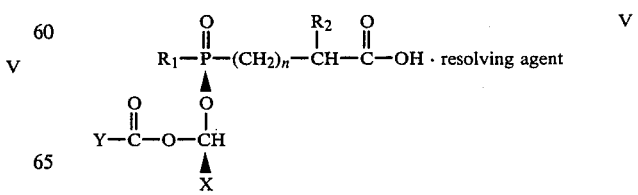 V such as

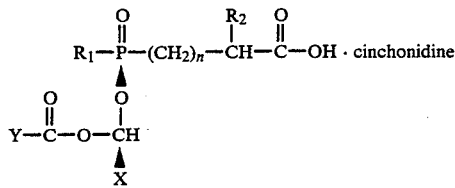

VA for example

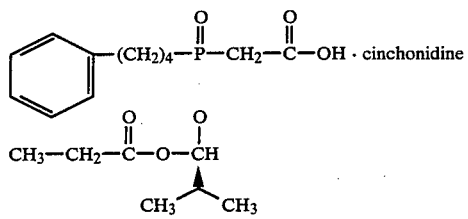

VA' are all novel compounds.

The starting phosphinic acid ester II

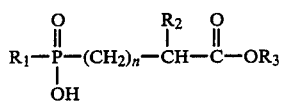

II is a known compound and may be prepared as described in U.S. Pat. No. 4,602,092; the phenylmethyl ester may be prepared as described in Example 1 of U.S. Pat. No. 4,602,092.

Alternatively, phosphinic acid ester II may be prepared by esterifying a phosphinic acid compound of the structure

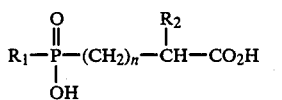

IVA (a) by treating the phosphinic acid compound IIA with an alcohol such as methanol or ethanol, or benzyl alcohol, with benzyl alcohol being preferred, at a temperature within the range of from about 25° to about 130° C. for a period of from about 2 to about 10 hours or (b) by treating the phosphinic acid compound IIA with an alkylchloroformate, such as ethyl or methyl chloroformate, or an arylalkylchloroformate, such as benzylchloroformate, with benzyl chloroformate preferred, in the presence of a base, such as triethylamine, pyridine or N,N-dimethylamine, an organic solvent such as toluene, and tetrahydrofuran or dioxane, the above reaction (b) being carried out at a temperature of within the range of from about −30° C. to about 30° C. for a period of from about 1 to about 4 hours.

In carrying out the above reactions (a) or (b), the phosphinic acid compound IIA will be employed in a molar ratio to the alcohol or chloroformate compound of within the range of from about 0.2:1 to about 1:1 and preferably from about 0.5:1 to about 1:1.

The term "aryl", as used throughout the specification either by itself or as part of a larger group, refers to phenyl or naphthyl, or phenyl or naphthyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" or "lower alkyl" as used throughout the specification either by itself or as part of a larger group, refers to groups having 1 to 10 carbon atoms and may include 1 or 2 halogen (Cl, I, Br or CF$_3$), lower alkoxy, aryl or cycloalkyl substituents. Alkyl groups having 1 to 4 carbon atoms are preferred.

The term "cycloalkyl", as used throughout the specification either by itself or as part of a larger group, refers to groups having 3 to 7 carbon atoms, such as cyclopropyl, cyclobutyl, cyclopentyl, cyclohexyl or cycloheptyl.

The term "alkoxy" or "alkylthio" as used throughout the specification either by itself or as part of a larger group, refers to groups having 1 to 8 carbon atoms. Alkoxy or alkylthio groups having 1 to 3 carbon atoms are preferred.

The term "arylalkyl" or "cycloalkylalkyl", as used throughout the specification either by itself or as part of a larger group, refers to an "alkyl" group as defined above containing an "aryl" or "cycloalkyl" substituent.

The phosphinic acid compound IA may be employed to prepare ACE inhibitors as disclosed in U.S. Pat. No. 4,337,201 such as

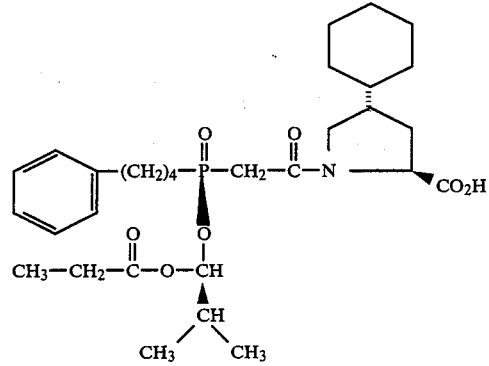

VII by reacting a phosphinic acid IA, such as

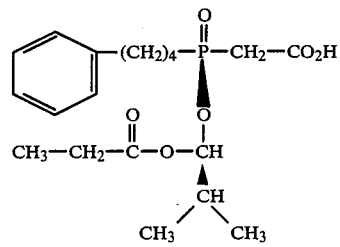

IA' with a compound of the structure

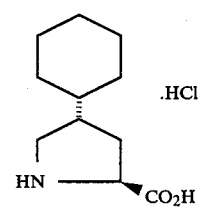

VIII or the free amino acid, in the presence of a coupling agent such as N,N'-dicyclohexylcarbodiimide, a mixed anhydride reagent such as pivaloyl chloride, carbonyldiimidazole or a mercaptobenztriazole or other conventional coupling agent, and an activating agent such as N-hydroxysuccinimide or hydroxybenzotriazole and optionally in the presence of a base such as diisopropylethylamine or triethylamine and recovering the desired compound from the reaction mixture.

The above reaction is carried out employing a molar ratio of IA', to VII of within the range of from about 0.5:1 to about 2:1, at a temperature within the range of from about −20° to about 30° C. for a period of from about 2 to about 12 hours.

Examples of phosphinic acid esters II useful as starting materials in carrying out the present invention, include, but are not limited to:

-continued $$X-\underset{\underset{H}{|}}{\overset{\overset{Hal}{|}}{C}}-O-\overset{\overset{O}{\|}}{C}-Y$$

| X | Y | Hal |
|---|---|---|
| C$_6$H$_5$ | C$_6$H$_5$ | Cl |
| | —(CH$_2$)$_2$— | Br |
| | —(CH$_2$)$_3$— | Br |
| | —CH=CH— | Br |
| 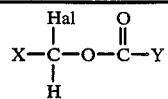 | | Cl |

$$R_1-\overset{\overset{O}{\|}}{\underset{\underset{OH}{|}}{P}}-(CH_2)_n-\overset{\overset{R_2}{|}}{C}H-\overset{\overset{O}{\|}}{C}-OR_3$$

| R$_1$ | n | R$_2$ | R$_3$ |
|---|---|---|---|
| C$_2$H$_5$ | 0 | H | —CH$_2$—C$_6$H$_4$—p-C$_2$H$_5$ |
| C$_3$H$_7$ | 1 | CH$_3$ | —CH$_2$—C$_6$H$_5$ |
| C$_6$H$_5$ | 0 | C$_6$H$_5$CH$_2$— | —CH$_2$—C$_6$H$_4$—p-CH$_3$ |
| C$_6$H$_5$CH$_2$— | 1 | C$_2$H$_5$ | —CH$_2$C$_6$H$_5$ |
| C$_6$H$_5$(CH$_2$)$_4$— | 0 | H | —CH$_2$—C$_6$H$_5$ |
|  | 1 | CH$_3$ | —CH$_2$—C$_6$H$_4$—o-CH$_3$ |
|  | 0 | H | —CH$_2$—C$_6$H$_4$—p-N(CH$_3$)$_2$ |
| 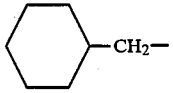 | 1 | C$_2$H$_5$ | —CH$_2$—C$_6$H$_4$—p-OCH$_3$ |
| 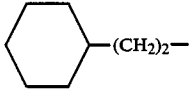 | 0 | H | —CH—C$_6$H$_5$<br>$\quad\,$\|<br>$\quad\,$CH$_3$ |
| 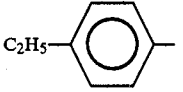 | 1 | C$_6$H$_5$CH$_2$— | —CH$_2$—C$_6$H$_4$—m-$\overset{\overset{O}{\|}}{C}$—CH$_3$ |

Examples of halo esters III suitable for use herein include but are not limited to $$X-\underset{\underset{H}{|}}{\overset{\overset{Hal}{|}}{C}}-O-\overset{\overset{O}{\|}}{C}-Y$$

| X | Y | Hal |
|---|---|---|
| CH$_3$ | H | Cl |
| C$_6$H$_5$ | CH$_3$ | Br |
| H | C$_6$H$_5$ | I |
| C$_2$H$_5$ | CH$_3$O | F |

The following working Examples represent preferred embodiments of the present invention. Unless otherwise indicated, all temperatures are expressed in degrees Centigrade.

EXAMPLE 1

[[2-Methyl-1-(1-oxopropoxy)propoxy](4-phenylbutyl)-phosphinyl]acetic acid (isomer B), cinchonidine salt (1:1)

A.

[Hydroxy(4-phenylbutyl)phenylbutyl)phosphinyl]acetic acid, phenylmethyl ester

To a solution of 4-phenylbutyl phosphinic acid (2.0 g, 0.01 mole) in chloroform (40 ml) was added triethylamine (3.2 ml, 0.022 mole) and the mixture was cooled in an ice bath to 0° C. Trimethylsilyl chloride (2.8 ml, 0.022 mole) was added to the above solution dropwise, followed by benzyl bromoacetate (1.6 ml, 0.011 mole). The ice bath was removed and the mixture stirred at room temperature for 5 hours and poured into 10% aqueous HCl (30 ml) and crushed ice (20 g). After shaking the mixture in a separatory funnel, the chloroform layer was separated and the aqueous layer was extracted with dichloromethane (2×50 ml). The combined organic phase was washed with brine, dried over anhydrous sodium sulfate and the solvents removed on a rotavap. The resulting crude thick oil (3.5 g) was dissolved in 30 ml ether, hexane was added dropwise to get a turbid solution and the mixture was left at room temperature overnight to complete the crystallization. It was cooled in the freezer for 2 hours, filtered and the solid was washed very thoroughly with hexane (50 ml), ether (50 ml) and again hexane (50 ml), ether (50 ml) in that order. The solid was vacuum dried to get 2.48 g (71%) of title compound, m.p. 68°–70° C. TLC. Silica gel, $CH_2Cl_2$:MeOH:HOAc (20:1:1) shows a single spot at $R_f 0.25$.

Anal Calcd for $C_{19}H_{23}O_4P$: C, 65.88; H, 6.69; P. 8.94. Found: C, 65.88; H, 6.77; P, 8.5.

B.

[[2-Methyl-1-(1-oxopropoxy)propoxy](4-phenylbutyl)-phosphinyl]acetic acid, phenyl methyl ester A solution of 50 g (0.14 mole) of Part A ester compound in 300 ml of dry $CHCl_3$ was treated with 28.6 g (0.28 mole) of $Et_3N$, 35.6 g (0.21 mole) of 1-chloroisobutyl propionate, 12.0 g (0.035 mole) of $(n-Bu)_4NHSO_4$ and 5.3 g (0.035 mole) of NaI.

The above mixture was stirred and heated to mild reflux for 20 hours, then cooled and the solvent evaporated in vacuo. The oil residue was dissolved in 150 ml of ether and washed with 150 ml of $H_2O$. The aqueous wash was extracted with 150 ml of ether (4×). The combined ether solutions were washed with 5% $NaHCO_3$ (3×150 ml), 10% $NaHSO_3$ and brine. After drying ($MgSO_4$) the ether was evaporated in vacuo to give 57.0 g (83%) of crude oil product.

Anal Calcd for $C_{26}H_{35}O_6P$: C, 65.80, H, 7.43. Found: C, 64.56; H, 7.40.

C.

[[2-Methyl-1-(1-oxopropoxy)propoxy](4-phenylbutyl)-phosphinyl]acetic acid (Pair of racemic mixtures or mixture of diastereomers)

A solution of 57.0 g (0.12 mole) of Part B compound in 300 ml of ethyl acetate was treated with 3.0 g of 10% Pd/C and hydrogenated on the Parr apparatus (45 psi) for 4 hours. The mixture was filtered through Hyflo and the solution was extracted with 5% $NaHCO_3$ (3×150 ml). The aqueous extracts were washed with ether, cooled to 5° and treated with 36 ml of HOAc. The product was extracted into ethyl acetate (2×200 ml), dried ($MgSO_4$) and the solvent was evaporated in vacuo. The residue was dissolved in 300 ml of toluene and the solvent was evaporated in vacuo to remove last traces of HOAc. The oil residue became semi-solid on standing at room temperature. The yield was 39.8 g (72% from Part A ester).

Anal Calcd for $C_{19}H_{29}O_6P$: C, 59.36; H, 7.60. Found: C, 59.30; H, 7.62.

D.

[[2-Methyl-1-(1-oxopropoxy)propoxy](4-phenylbutyl)-phosphinyl]acetic acid (A/B isomer, racemic mixture)

A suspension of 10.0 g (0.026 mole) of Part C compound mixture in 50 ml of isopropyl ether was stirred vigorously for 15 minutes, then kept at 5° for 20 hours.

The colorless product was filtered, washed with a small amount of cold isopropyl ether to give 5.0 g of A/B isomer, m.p. 87°–89° C. The filtrate was evaporated in vacuo and retained for isolation of isomer C/D.

A solution of the above material in 110 ml of hot isopropyl ether was filtered through a hot glass funnel (glass wool). The cooled solution gave 4.6 g (92%) of desired product, m.p. 90°–92°.

E.

[[2-Methyl-1-(1-oxopropoxy)propoxy](4-phenylbutyl)-phosphinyl]acetic acid (Resolution; isomer B), cinchonidine salt (1:1)

To a vigorously stirred suspension of 980 g (3.33 mol) of l-cinchonidine in 6 L of ethyl acetate maintained at 45° C. was gradually added 1275.5 g (3.33 mol) of Part A/B isomer mixture and stirring then continued for an additional 2.5 hours while the resulting suspension of salt was gradually heated to 70° C. when complete solution was obtained. After filtration (Hyflo) from a small amount of insoluble material, the solution was seeded and cooled. The crystalline product which separated was then filtered, washed with 1200 ml of 1:1 ethyl acetate/isopropyl ether, and dried in vacuo to give 1897.2 g of cinchonidine salt enriched in the B-isomer, m.p. 106°–109° C., $[\alpha]_D = -59.3°$ (c=1, methanol), $[\alpha]_{365} = -237.6°$ (c=1, methanol). This material was combined with 136.8 g of similarly prepared material (from 0.412 mol of Part D A/B isomer) and the total quantity (2014 g) recrystallized from 10.18 L of boiling ethyl acetate to afford after filtration, washing with 1500 ml of the same solvent mixture used before, and drying in vacuo 1162 g (92%) of the title B-isomer cinchonidine salt, m.p. 120°–122° (dec.), $[\alpha]_D = -45°.2°$ (c=1, methanol), $[\alpha]_{365} = -185.5°$ (c=1, methanol).

A sample (10 g) was recrystallized twice from acetonitirle and three times from ethyl acetate additionally to give salt of m.p. 125°–126° (dec.), $[\alpha]_D = -42.2°$, $[\alpha]_{360} = -178.8°$, $R_f 0.38$ ($SiO_2$-$CHCl_3$/MeOH, 1:9).

Anal Calcd for $C_{19}H_{29}O_6P \cdot C_{19}H_{22}N_2O$: C, 67.23; H; 7.57; N, 4.13. Found: C, 67.17; H; 7.62; N, 4.14.

EXAMPLE 2

[[2-Methyl-1-(1-oxopropoxy)propoxy](4-phenylbutyl)-phosphinyl]acetic acid

A. [Hydroxy(4-phenylbutyl)phosphinyl]acetic acid, phenylmethyl ester

To a well stirred solution of [hydroxy-(4-phenylbutyl)phosphinyl]acetic acid (prepared as described in Example 23 of U.S. Pat. No. 4,602,092) (422.5 g, 1.65 mole) in tetrahydrofuran (4700 ml, alumina purified)

maintained at −5° C. to −10° C. was gradually added triethylamine (290 ml, 2.08 mole). This was then followed by the dropwise addition of a solution of benzylchloroformate (275 ml, 1.93 mole) in purified tetrahydrofuran (1320 ml). After removing the cooling bath, stirring was continued for three hours. After this time, the reaction mixture was filtered. The solids were washed with ethyl acetate (2×1000 ml). The combined filtrates were concentrated in vacuo. The resultant residue was dissolved in ethyl acetate (4000 ml) and washed with water (2×1000 ml), 2.5% hydrochloric acid (2×600 ml) and brine (2×1000 ml). The organic phase was dried over magnesium sulfate, filtered and concentrated. The residue was triturated with 1:1 ether/hexane (2×500 ml) and collected by filtration. The solid was washed on the frit with 1:1 ether/hexane then dried in vacuo at 30° C. overnight to yield 509 g of colorless crystalline product m.p. 68°–70° C.

Anal. Calcd for $C_{19}H_{23}O_4P$: C, 65.89; H, 6.69; P, 8.94. Found: C, 65.80; H, 6.80; P, 9.10.

B. 1-chloroisobutyl propionate

To a vigorously stirred, ice-cooled solution of propionyl chloride (1407 g, 14.8 moles) in 3A sieve-dried chloroform (3000 ml) was added zinc chloride (7.4 g) followed by the dropwise addition (exotherm) of isobutyraldehyde (1132 g, 14.8 moles) at such a rate that the temperature was maintained at 25° C. (three hours).

The reaction mixture was stirred for 30 minutes additional with continued ice cooling. The ice bath was then removed and stirring continued for one hour. The reaction mixture was then washed with water (3×1500 ml) and brine (1×1500 ml). After drying over $MgSO_4$ the organic layer was filtered and concentrated in vacuo. The residual oil was distilled to yield 2269 g of colorless liquid, b.p. 46°–48° C. (4.5 mm).

C.
[[2-Methyl-1-(1-oxopropoxy)propoxy](4-phenylbutyl)phosphinyl]acetic acid

To a stirred suspension of Example 1 Part E salt (406.8 g, 0.6 mole) in a mixture of ethyl acetate (4800 ml) and water (2700 ml) was added dropwise a solution of potassium hydrogen sulfate (180 g) in water (700 ml) to a pH of 2.3. The organic layer was separated, washed with brine (1×1000 ml) and dried over magnesium sulfate (2 hours). The combined aqueous phases were reextracted with ethyl acetate (3×1500 ml) and treated as above. The combined ethyl acetate washes were filtered and concentrated in vacuo. The residue was azeotroped with toluene (3×1300 ml) then dried in vacuo for three days to yield 230.4 g of the title liberated acid.

EXAMPLE 3
[1(±)4S]-4-Cyclohexyl-1-[[[2-methyl-1-(1-oxopropoxy)propoxy](4-phenylbutyl)phosphinyl]acetyl]-L-proline, monosodium salt (isomer B)

A slurry of Example 2 acid, dried in vacuo at room temperature for 72 hours, (230.4 g, 0.6 moles) and hydroxybenzotriazole hydrate, dried, in vacuo at 80° C. for 24 hours, (101.1 g, 0.66 mole) in Burdick & Jackson dichloromethane (sieved dried) (6 l) was chilled in an ice/acetone bath and treated with N,N-dicyclohexylcarbodiimide (DCC) (136 g, 0.66 mole). The mixture was warmed to room temperature and stirred for 3 hours. The mixture was then chilled in ice/acetone and treated with (trans)-4-cyclohexyl-L-proline, hydrochloride compound (154.2 g, 0.66 mole) followed by diisopropylethylamine (170.7 g, 1.32 mole). The reaction mixture was stirred at room temperature for 18 hours. The mixture was then chilled, treated with water (1 l) and concentrated in vacuo to remove dichloromethane. The residue was diluted with ether (3600 ml) and water (3600 ml) and filtered. The filtrate was brought to pH=1.8 with 10% hydrochloric acid. The ether layer was separated and the aqueous layer washed with ethyl acetate (3×2 l). The combined organic layers were washed with 5% $KHSO_4$ (3×1 l), water (3×1 l) and brine (1 l), dried over magnesium sulfate and concentrated in vacuo to yield 398.9 g of crude product.

The crude product was dissolved in acetone (4393 ml), treated with a solution of 2-ethyl hexanoic acid, sodium salt (117.3 g) in acetone (1468 ml), then stirred at room temperature overnight. The resultant precipitate was collected by filtration, washed with acetone (3×400 ml) and hexane (1 l) then dried in vacuo. Yield 277 g, m.p. 195°–196° C. $[\alpha]_D=-5.1°$ (MeOH, c=2) HI=99.8%. Isomer "A" was not detectable.

The total amount of title product was obtained by combining the products obtained from 4 separate coupling reactions and subsequent sodium salt drops using Example 2 acid (runs of 38.4 g, 115 g, 230 g, and 230 g). The combined solids from the four runs were reslurried in 4000 ml of isopropyl alcohol (preheated to 40° C.) then stirred vigorously at 40° C. for 15 minutes. The slurry was cooled to room temperature and filtered, an extremely slow filtration taking almost 6 hours. The cake was washed with additional isopropyl alcohol then ether. The solid was dried in vacuo at room temperature to yield 710 g of title product. M.P. 195°–196° C. $[\alpha]_D=-5.1°$ (MeOH, c=2) HI=99.9. Isomer "A" was not detectable.

EXAMPLE 4
[Hydroxy(4-phenylbutyl)phosphinyl]acetic acid, phenylmethyl ester

[Hydroxy-(4-phenylbutyl)phosphinyl]acetic acid (5 g), benzyl alcohol (2.21 g) and a catalytic amount of p-toluene sulfonic acid (44 mg) are combined in 18.75 ml of toluene. The mixture is heated to reflux (+108° C.) and is maintained at reflux until HPLC analysis indicates no further consumption of he starting acid (about 7 hours). Water which is generated during the course of the reaction is allowed to settle from the reflux in a leg in the return system. After completion of the reaction, DARCO G-60 (2.2 g, 4.5 wt% based on starting acid) may be added to the batch at 80° C. to 95° C. if the starting acid is slightly off-color (tan). The DARCO is filtered from the batch prior to crystallization.

The clear reaction solution is cooled to 60° C. and heptane (19.53 ml) is added to the batch to allow crystallization. The batch is cooled to the crystallization temperature (25° C. to 29° C.) and held at that temperature for at least 90 minutes. The resultant slurry is cooled to 0° C. to 5° C. and held at that temperature for at least 2 hours prior to filtration. The filter cake is washed with 3×0.5 cake volumes of heptane:toluene (2:1 by volume). The crystalline product is dried under vacuum at 40° C. until the residual solvent is less than 0.5 wt%.

The yield of this process is about 88 M%.

Should the title compound need to be recrystallized, it is dissolved in 10 ml of methyl isobutyl ketone at 55°

C. to 60° C. The solution is polish filtered and is cooled to 25° C. to 30° C. to induce crystallization of the acid title compound. The slurry is then cooled to 0° C. to 5° C. and filtered. The filter cake is washed with 2×0.5 cakes volumes of chilled (0° C. to 5° C.) methyl isobutyl ketone. The product is dried at 35° C. under vacuum until there is no evidence of residual solvent.

EXAMPLE 5

[[2-Methyl-1-(1-oxopropoxy)propoxy](4-phenylbutyl)-phosphinyl]acetic acid 4 g of Example 4 compound is refluxed (112° C.) with 2.34 g of triethylamine and 3.80 g of Example 2 Part B ester in 12 ml of toluene for approximately 8 hours to form the benzyl ester of the title acid. After cooling, the triethylamine hydrochloride salt is filtered off and the rich toluene filtrate is treated with hydrogen and 0.2 g of 5% (50% water wet) palladium on carbon to deprotect the benzyl ester.

After filtering off the catalyst, the product is extracted into 16 ml of 5% sodium bicarbonate solution. The rich aqueous is acidified to pH 3.0 with approximately 1.32 ml of concentrated HCl, and then the product is extracted into 16 ml of isobutyl acetate (IBA). Title acid (the IA/IB isomer pair) is isolated as a wet crystalline solid by concentrating and cooling the IBA.

The wet cake is recrystallized from methyl isobutyl ketone (MIBK) to give a product (1.3 g) which contains 0.1% or less of the IC/ID isomer pair.

What is claimed is:

1. A compound having the structure $$R_1-\overset{O}{\underset{\underset{\underset{X}{\overset{|}{CH}}}{\overset{|}{O}}}{\overset{\|}{P}}}-(CH_2)_n-\overset{R_2}{\underset{|}{CH}}-\overset{O}{\overset{\|}{C}}-OH$$

$$Y-\overset{O}{\overset{\|}{C}}-O$$

including salts thereof, and all stereoisomers thereof, wherein $R_1$ is lower alkyl, aryl, arylalkyl, cycloalkyl or cycloalkylalkyl;

$R_2$ is hydrogen, lower alkyl or arylalkyl;

X is hydrogen, lower alkyl or phenyl;

Y is hydrogen, lower alkyl, phenyl or alkoxy or together X and Y are $-(CH_2)_2$, $-(CH_2)_3-$, $-CH=CH$ or

[structure of methylphenyl group];

and
n is 0 or 1.

2. The compound as defined in claim 1 in the form of the L-cinchonidine salt thereof.

3. The compound as defined in claim 1 wherein $R_1$ is arylalkyl, n is 0, $R_2$ is hydrogen, X is lower alkyl and Y is lower alkyl.

4. The compound as defined in claim 3 having the structure

[structure showing phenyl-(CH2)4-P(=O)(O-CH(OC(=O)CH2CH3)(between CH3 and CH3))-CH2-C(=O)-OH.cinchonidine]

5. The compound as defined in claim 3 having the structure

[structure showing phenyl-(CH2)4-P(=O)(O-CH(OC(=O)CH2CH3)(between CH3 and CH3))-CH2-C(=O)-OH]

6. A compound having the structure $$R_1-\overset{O}{\underset{\underset{\underset{H}{\overset{|}{C}}}{\overset{|}{O}}}{\overset{\|}{P}}}-(CH_2)_n-\overset{R_2}{\underset{|}{CH}}-\overset{O}{\overset{\|}{C}}-OR_3$$

$$X-\overset{O}{\overset{\|}{C}}-O$$

including all stereoisomers thereof, wherein $R_1$ is lower alkyl, aryl, arylalkyl, cycloalkyl or cycloalkylalkyl;

$R_2$ is hydrogen, lower alkyl or arylalkyl;

$R_3$ is benzyl, $-\underset{\underset{alkyl}{|}}{CH}-$[phenyl], or $-CH_2-$[phenyl with $R'_3$]

wherein $R'_3$ is alkyl, alkoxy, alkanoyl, phenyl or dialkylamino;

X is hydrogen, lower alkyl or phenyl;

Y is hydrogen, lower alkyl, phenyl or alkoxy, or together X and Y are $-(CH_2)_2$, $-(CH_2)_3-$, $-CH=CH$ or

[structure of methylphenyl group];

and
n is 0 or 1.

7. The compound as defined in claim 6 wherein $R_3$ is hydrogen or benzyl.

8. The compound as defined in claim 7 having the structure

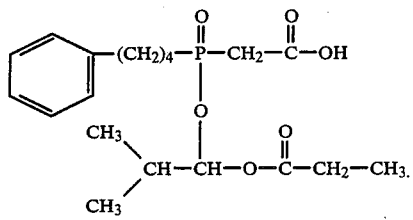
9. The compound as defined in claim 7 having the structure
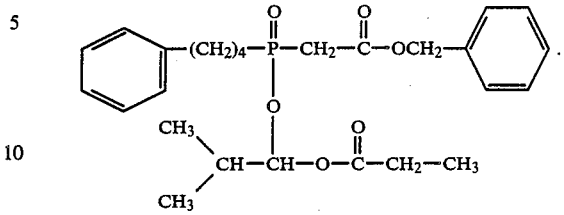
* * * * *